United States Patent
Von Hagen

(10) Patent No.: US 10,563,169 B2
(45) Date of Patent: *Feb. 18, 2020

(54) CELL CULTURE MEDIA

(71) Applicant: MERCK PATENT GMBH, Darmstadt (DE)

(72) Inventor: Joerg Von Hagen, Pfungstadt (DE)

(73) Assignee: Merck Patent GmbH, Darmstadt (DE)

( * ) Notice: Subject to any disclaimer, the term of this patent is extended or adjusted under 35 U.S.C. 154(b) by 257 days.

This patent is subject to a terminal disclaimer.

(21) Appl. No.: 15/534,230

(22) PCT Filed: Nov. 13, 2015

(86) PCT No.: PCT/EP2015/002274
§ 371 (c)(1),
(2) Date: Jun. 8, 2017

(87) PCT Pub. No.: WO2016/091349
PCT Pub. Date: Jun. 16, 2016

(65) Prior Publication Data
US 2017/0342372 A1    Nov. 30, 2017

(30) Foreign Application Priority Data
Dec. 11, 2014  (EP) .................. 14004169

(51) Int. Cl.
*C12N 5/00*    (2006.01)
(52) U.S. Cl.
CPC ........ *C12N 5/0037* (2013.01); *C12N 2500/12* (2013.01); *C12N 2500/30* (2013.01); *C12N 2500/32* (2013.01); *C12N 2500/35* (2013.01)

(58) Field of Classification Search
None
See application file for complete search history.

(56) References Cited

FOREIGN PATENT DOCUMENTS

EP    2674482 A1    12/2013

OTHER PUBLICATIONS

Joerg Von Hagen: "Development of novel chemically defined media for CHO cell applicatio . . . ", Jan. 1, 2013 (Jan. 1, 2013), XP055240357, Retrieved from the Internet [retrieved on Jan. 12, 2016].
Anonymous: "Cell Culture Media—Addressing Variability in Dry Powder Mammalian Cell Culture Media | Articles | drug development and delivery back issues | Drug Development & Delivery", Jun. 1, 2013 (Jun. 1, 2013), XP055194700, Retrieved from the Internet [retrieved on Jun. 10, 2015].
Aline Zimmer: "Effect of raw materials and production processes on dry powder media . . . ", Cell Culture World Congress, Feb. 29, 2012 (Feb. 29, 2012), XP055240359, Retrieved from the Internet [retrieved on Jan. 12, 2016].
PCT/EP2015/002274 search report dated Jan. 21, 2016.

*Primary Examiner* — Renee Claytor
*Assistant Examiner* — Trent R Clarke
(74) *Attorney, Agent, or Firm* — Millen White Zelano and Branigan, PC; Csaba Henter

(57) ABSTRACT

The present invention relates to dry cell culture media comprising amino acid components of certain particle size. Some dry powder cell culture media show poor dissolving properties and result in turbid solutions when they are dissolved in aqueous solutions. Using amino acid components of certain particle sizes significantly reduces that problem.

10 Claims, No Drawings

CELL CULTURE MEDIA

The present invention relates to dry cell culture media comprising amino acid components of certain particle size. Some dry powder cell culture media show poor dissolving properties and result in turbid solutions when they are dissolved in aqueous solutions. Using amino acid components of certain particle sizes significantly reduces that problem.

Cell culture media in aqueous solution can provide an environment which supports and maintains the growth of cells and/or maintains a desired physiological cellular condition adventitious to the targeted production of certain products.

Cell culture media comprise of a complex mixture of components, sometimes more than one hundred different components, depending on the type of organism whose growth and/or targeted physiological status shall be supported.

The cell culture media required for the propagation of mammalian, insect or plant cells are typically much more complex than the media to support the growth of bacteria, yeast or fungi.

The first cell culture media that were developed were complex media consisting of diverse mixtures of components which were very poorly chemically defined, poorly characterized and difficult to manufacture with a consistent quality, such as plasma, serum, embryo extracts, and/or other biological extracts or peptones. A major advance was thus made with the development of chemically defined media. Chemically defined media often comprise of but are not exclusively limited to amino acids, vitamins, metal salts, antioxidants, chelators, growth factors, buffers, hormones, and many more substances known to those expert in the art.

Some cell culture media are offered as sterile aqueous liquids. The disadvantage of liquid cell culture media is their reduced shelf life and difficulties for shipping and storage. As a consequence, many cell culture media are presently offered as finely milled dry powder mixtures. These are manufactured for the purpose of dissolving in water and/or aqueous solutions and in the dissolved state are designed, often with other supplements, for supplying cells with a substantial nutrient base for growth and/or production of biopharmaceuticals from said cells and/or used as a feed to supply cells when specific nutrients become limiting.

A limiting factor for the preparation and the use of cell culture media from dry powder is the poor solubility of some components resulting in turbid media. An amendment of the media composition or substitution of certain components is often unwanted. A mere reduction of the overall particle size of the media components does not lead to an improvement.

Consequently it would be favourable to find a way to improve the overall solubility of a given media composition.

It has been found that the particle size of the amino acid components of a dry cell culture medium significantly influences its dissolving properties.

Improved dissolving properties can be found for media in which certain amino acids are present in particle sizes between 10 and 50 μm and others in particle sizes between 50 and 150 μm.

The present invention is therefore directed to a dry cell culture medium in which more than 70% (w/w), preferably more than 80% (w/w) of all cysteine, cystine and tyrosine present in the medium is present in the form of particles with particle sizes below 50 μm and in which more than 70% (w/w), preferably more than 80% (w/w) of all serine, iso-leucine, leucine, glycine and phenylalanine are present in the form of particles with particle sizes above 100 μm.

In a preferred embodiment, more than 70% (w/w), preferably more than 80% (w/w) of all arginine, aspartic acid, glutamic acid and threonine present in the medium is present in the form of particles with particle sizes between 50 and 150 μm.

In a preferred embodiment, in addition, more than 60% (w/w), preferably more than 75% (w/w) of all histidine is present in particle sizes between 25 and 100 μm.

In one embodiment the cell culture medium is a mammalian cell culture medium.

In another embodiment, the cell culture medium is a chemically defined cell culture medium.

In a preferred embodiment, at least 70% (w/w), preferably at least 80% (w/w) most preferred at least 90% (w/w) of all cysteine, cystine and tyrosine present in the medium is present in the form of particles with particle sizes between 10 and 50 μm.

In another preferred embodiment, more than 70%, preferably more than 80% (w/w) of all other amino acids beside cysteine, cystine, tyrosine, arginine, aspartic acid, glutamic acid, histidine and threonine are present in the form of particles with particle sizes above 100 μm, preferably above 150, most preferred above 180 μm.

The present invention is further directed to a method for producing a cell culture medium by
a) providing cystein, cystine and tyrosine,if present,in the form of particles of which more than 70% (w/w) have particle sizes below 50 μm and arginine, aspartic acid, glutamic acid and threonine, if present, in the form of particles of which more than 70% (w/w) have particle sizes between 50 and 150 μm and histidine if present in the form of particles of which more than 60% (w/w) have particle sizes between 25 and 100 μm as well as optionally further amino acids in the form of particles of which more than 70% (w/w) have particle sizes above 150 μm
b) providing all other media components beside the ones provided in step a) and mixing, sieving and milling them
c) mixing the components provided in step a) and step b)

The present invention is further directed to a process for culturing cells by
a) providing a bioreactor
b) mixing the cells to be cultured with a cell culture medium according to the present invention and optionally water or an aqueous buffer.
c) incubating the mixture of step b).

A cell culture medium according to the present invention is any mixture of components which maintains and/or supports the in vitro growth of cells and/or supports a particular physiological state. It might be a complex medium or a chemically defined medium. The cell culture medium can comprise all components necessary to maintain and/or support the in vitro growth of cells or only some components so that further components are added separately. Examples of cell culture media according to the present invention are full media which comprise all components necessary to maintain and/or support the in vitro growth of cells as well as media supplements or feeds. In a preferred embodiment the cell culture medium is a full medium or a medium which lacks few components.

Typically, the cell culture media according to the invention are used to maintain and/or support the growth of cells and/or to support a particular physiological state in a bioreactor.

A mammalian cell culture medium is a mixture of components which maintain and/or support the in vitro growth of mammalian cells. Examples of mammalian cells are human or animal cells, preferably CHO cells, COS cells, I VERO cells, BHK cells, AK-1 cells, SP2/0 cells, L5.1 cells, hybridoma cells or human cells.

Chemically defined cell culture media are cell culture media that do not comprise any chemically undefined substances. This means that the chemical composition of all the chemicals used in the media is known. The chemically defined media do not comprise any yeast, animal or plant tissues; they do not comprise feeder cells, serum, extracts or digests or other components which may contribute chemically poorly defined proteins and/or peptides and/or hydrolysates to the media. Chemically undefined or poorly defined chemical components are those whose chemical composition and structure is not well known, are present in poorly defined and varying composition or could only be defined with enormous experimental effort—comparable to the evaluation of the chemical composition and structure of a protein like albumin or casein.

A powdered cell culture medium or a dry powder medium is a cell culture medium typically resulting from a milling process or a lyophilisation process. That means the powdered cell culture medium is a granular, particulate medium—not a liquid medium. The term "dry powder" may be used interchangeably with the term "powder;" however, "dry powder" as used herein simply refers to the gross appearance of the granulated material and is not intended to mean that the material is completely free of complexed or agglomerated solvent unless otherwise indicated.

Cells to be cultured with the media according to the present invention may be prokaryotic cells like bacterial cells or eukaryotic cells like yeast, fungi, plant or animal cells. The cells can be normal cells, immortalized cells, diseased cells, transformed cells, mutant cells, somatic cells, germ cells, stem cells, precursor cells or embryonic cells, any of which may be established or transformed cell lines or obtained from natural sources.

The size of a particle means the diameter of the particle. The particle diameter is determined by laser light scattering in silicone oil. Using this technique, the particle size is reported as a volume equivalent sphere diameter.

An inert atmosphere is generated by filling the respective container or apparatus with an inert gas. Suitable inert gases are noble gases like argon or preferably nitrogen. These inert gases are minimally-reactive and prevent undesirable chemical reactions from taking place. In the process according to the present invention, generating an inert atmosphere means that the concentration of oxygen is reduced below 10% (v/v) absolute, e.g. by introducing liquid nitrogen or nitrogen gas.

Different types of mills are known to a person skilled in the art.

A pin mill, also called centrifugal impact mill, pulverizes solids whereby protruding pins on high-speed rotating disks provide the breaking energy. Pin mills are for example sold by Munson Machinery (USA), Premium Pulman (India) or Sturtevant (USA).

A jet mill uses compressed gas to accelerate the particles, causing them to impact against each other in the process chamber. Jet mills are e.g. sold by Sturtevant (USA) or PMT (Austria).

A fitz mill commercialized by Fitzpatrick (USA), uses a rotor with blades for milling.

A process that is run continuously is a process that is not run batchwise. If a milling process is run continuously it means that the media ingredients are permanently and steadily fed into the mill over a certain time.

The cell culture full media according to the present invention typically comprise at least one or more saccharide components, one or more amino acids, one or more vitamins or vitamin precursors, one or more salts, one or more buffer components, one or more co-factors and one or more nucleic acid components. The composition of feed media greatly varies depending on the components that need to be added to the cell culture. The media may also comprise sodium pyruvate, insulin, vegetable proteins, digests or extracts, fatty acids and/or fatty acid derivatives and/or pluronic product components (block copolymers based on ethylene oxide and propylene oxide) in particular Poloxamer 188 sometimes called Pluronic F 68 or Kolliphor P 188 or Lutrol F 68 and/or surface active components like chemically prepared non-ionic surfactants. One example of a suitable non-ionic surfactant are difunctional block copolymer surfactants terminating in primary hydroxyl groups also called poloxamers, e.g. available under the trade name pluronic® from BASF, Germany.

Saccharide components are all mono- or di-saccharides, like glucose, galactose, ribose or fructose (examples of monosaccharides) or sucrose, lactose or maltose (examples of disaccharides).

Examples of amino acids according to the invention are the proteinogenic amino acids, especially the essential amino acids, Examples of amino acids are alanine, cysteine, cystine, aspartic acid, glutaminic acid, phenylalanine, glycine, histidine, isoleucine, lysine, leucine, methionine, asparagine, proline, hydroxyproline, glutamine, arginine, serine, threonine, valine, tryptophan and tyrosine. According to the invention, the name of the amino acid like "tyrosine" means the D- or L-form if applicable as well as the amino acid itself or any salt thereof, like the hydrochloride form or the sodium salt.

Examples of vitamins are Vitamin A (Retinol, retinal, various retinoids, and four carotenoids), Vitamin $B_1$ (Thiamine), Vitamin $B_2$ (Riboflavin), Vitamin $B_3$ (Niacin, niacinamide), Vitamin $B_5$ (Pantothenic acid), Vitamin $B_6$ (Pyridoxine, pyridoxamine, pyridoxal), Vitamin $B_7$ (Biotin), Vitamin $B_9$ (Folic acid, folinic acid), Vitamin $B_{12}$ (Cyanocobalamin, hydroxycobalamin, methylcobalamin), Vitamin C (Ascorbic acid), Vitamin D (Ergocalciferol, cholecalciferol), Vitamin E (Tocopherols, tocotrienols) and Vitamin K (phylloquinone, menaquinones). Vitamin precursors and analogues are also included.

Examples of salts are components comprising inorganic ions such as bicarbonate, calcium, chloride, magnesium, phosphate, potassium and sodium or trace elements such as Co, Cu, F, Fe, Mn, Mo, Ni, Se, Si, Ni, Bi, V and Zn. Examples are copper(II) sulphate pentahydrate ($CuSO_4.5H_2O$), sodium chloride (NaCl), calcium chloride ($CaCl_2.2H_2O$), potassium chloride (KCl), Iron(II)sulphate, sodium phosphate monobasic anhydrous ($NaH_2PO_4$), magnesium sulphate anhydrous ($MgSO_4$), sodium phosphate dibasic anhydrous ($Na_2HPO_4$), magnesium chloride hexahydrate ($MgCl_2.6H_2O$), zinc sulphate heptahydrate.

Examples of buffers are $CO_2/HCO_3$ (carbonate), phosphate, HEPES, PIPES, ACES, BES, TES, MOPS and TRIS.

Examples of cofactors are thiamine derivatives, biotin, vitamin C, NAD/NADP, cobalamin, vitamine B12, flavin mononucleotide and derivatives, glutathione, heme, nucleotide phophates and derivatives.

Nucleic acid components, according to the present invention, are the nucleobases, like cytosine, guanine, adenine, thymine or uracil, the nucleosides like cytidine, uridine, adenosine, guanosine and thymidine, and the nucleotides like adenosine monophosphate or adenosine diphosphate or adenosine triphosphate.

A medium might for example comprise one or more of the following compounds:

L-ASPARAGINE MONOHYDRATE
L-ISOLEUCINE
L-PHENYLALANINE
SODIUM L-GLUTAMATE MONOHYDRATE
L-LEUCINE
L-THREONINE
L-LYSINE MONOHYDROCHLORIDE
L-PROLINE
L-SERINE
L-ARGININE MONOHYDROCHLORIDE
L-HISTIDINE MONOHYDROCHLORIDE MONOHYDRATE
L-METHIONINE
L-VALINE
L-Tyrosine
L-Cysteine
L-Cystine
MONO-SODIUM-L-ASPARTATE-MONOHYDRATE
L-TRYPTOPHAN
CHOLINE CHLORIDE
MYO-INOSITOL
NICOTINAMIDE
CALCIUM-D(+) PANTOTHENATE
PYRIDOXINE HYDROCHLORIDE
THIAMINE CHLORIDE HYDROCHLORIDE
VITAMIN B12 (CYANOCOBALAMINE) MICRONIZED
BIOTIN
FOLIC ACID
RIBOFLAVIN
MAGNESIUM SULFATE ANHYDROUS
COPPER(II) SULFATE PENTAHYDRATE
ZINC SULFATE HEPTAHYDRATE
1,4-DIAMINOBUTANE DIHYDRCHLORIDE
AMMONIUM HEPTAMOLYBDATE TETRAHYDRATE
CADMIUM SULFATE HYDRATE
MANGANESE(II) CHLORIDE TETRAHYDRATE
NICKEL(II) CHLORIDE HEXAHYDRATE
SODIUM META SILICATE
SODIUM METAVANADATE
TIN(II) CHLORIDE DIHYDRATE
SODIUM SELENITE (ABOUT 45% SE)
SODIUM DIHYDROGEN PHOSPHATE MONOHYDRATE
AMMONIUM IRON(III) CITRATE (ABOUT 18% FE)

Freezing according to the present invention means cooling to a temperature below 0° C.

The gist of the present invention is to provide powdered cell culture media that can be easily processed without clumping. When the dry powder media are dissolved in a suitable solvent by admixing the powder and the solvent, the powder dissolves and produces a liquid cell culture medium such as a full medium, a medium supplement, a medium subgroup or a feed with a desired and homogenous concentration of the media components.

The simple dissolving of a powdered cell culture medium is often complicated by substances like tyrosine or cysteine/cystine which have a poor solubility in aqueous solvents. L-tyrosine for example has a solubility of 0.4 g/l in water at a temperature of 25° C. Cysteine easily forms the dimer cystine which is also poorly soluble. Other amino acids like glycine, valine, leucine, isoleucine and proline have moderate solubility in water.

It has been found that instead of simply reducing the particle size of the media components, it is much more efficient to not only reduce but adjust the particle size of certain amino acids, whereby tyrosine and cysteine should have a particle size below 50 μm and Ser, Gly, Ile, Leu and Phe should have a particle size above 100 μm. Other amino acids like Arg, Asp, Glu and Thr preferably have particle sizes between 50 and 150 μm, His preferably has a particle size between 25 and 100 μm.

It would of course be favorable to have 100% of the above mentioned amino acids present in the indicated particle size ranges. But the production of the amino acids with such particle size ranges would be very complicated. It has been found that the positive effect of the present invention is also measurable if at least around 70% (w/w) of the amino acid is present in the indicated particle size range. Amino acids with such a particle size distribution can typically be prepared by standard milling processes.

The powdered cell culture media of the present invention are preferably produced by mixing all components beside the amino acids which shall be added in the form of particles having a specific particle size, sieving and milling them. The mixing of the components is known to a person skilled in the art of producing dry powdered cell culture media by milling. Preferably, the components are thoroughly mixed so that all parts of the mixture have nearly the same composition. The higher the uniformity of the composition, the better the quality of the resulting medium with respect to homogenous cell growth.

The milling can be performed with any type of mill suitable for producing powdered cell culture media. Typical examples are ball mills, pin mills, fitz mills or jet mills. Preferred is a pin mill, a fitz mill or a jet mill, very preferred is a pin mill.

A person skilled in the art knows how to run such mills. A large scale equipment mill with a disc diameter of about 40 cm is e.g. typically run at 1-6500 revolutions per minute in case of a pin mill, preferred are 1-3000 revolutions per minute.

The milling can be done under standard milling conditions resulting in powders with particle sizes between 10 and 300 μm, most preferably between 25 and 100 μm.

Preferably, all components of the mixture which is subjected to milling are dry. This means, if they comprise water, they do only comprise water of crystallization but not more than 10%, preferably not more than 5% most preferred not more than 2% by weight of unbound or uncoordinated water molecules.

In a preferred embodiment, the milling is performed in an inert atmosphere. Preferred inert protective gas is nitrogen.

In another preferred embodiment, all components of the mixture are frozen prior to milling. Freezing of the ingredients prior to the milling can be done by any means that ensures a cooling of the ingredients to a temperature below 0° C. and most preferably below −20° C. In a preferred embodiment the freezing is done with liquid nitrogen. This means the ingredients are treated with liquid nitrogen, for example by pouring liquid nitrogen into the container in which the ingredients are stored prior to introduction into the mill. In a preferred embodiment, the container is a feeder. If the container is a feeder the liquid nitrogen is preferably introduced at the side or close to the side of the feeder at which the ingredients are introduced.

Typically the ingredients are treated with the liquid nitrogen over 2 to 20 seconds.

Preferably the cooling of the ingredients is done in a way that all ingredients that enter into the mill are at a temperature below 0° C., most preferred below −20° C.

In a preferred embodiment, all ingredients are put in a container from which the mixture is transferred in a feeder, most preferred in a metering screw feeder. In the feeder the ingredients are sometimes further mixed—depending on the type of feeder—and additionally cooled. The frozen mixture is then transferred from the feeder to the mill so that the mixture which is milled in the mill preferably still has a temperature below 0° C., more preferred below −20° C.

Typically the blending time, that means the residence time of the mixture of ingredients in the feeder is more than one minute, preferably between 15 and 60 minutes.

A metering screw feeder, also called dosage snail, is typically run at a speed of 10 to 200 revolutions per minute, preferably it is run at 40 to 60 revolutions per minute.

Typically, the temperature of the mill is kept between −50 and +30° C. In a preferred embodiment, the temperature is kept around 10° C.

The oxygen level during milling preferably is below 10% (v/v).

The process can be run e.g. batch-wise or continuously. In a preferred embodiment the process according to the present invention is done continuously by, over a certain time, permanently filling the mixture of ingredients into a feeder for cooling and permanently filling cooled mixture from the feeder into the mill.

The amino acids of certain particle sizes can also be produced by milling. Details about how to run a milling process can be found above. The amino acids are preferably milled in pin mill or jet mill systems.

The amino acids are then added to the other media components and are preferably thoroughly mixed with the other components e.g. using the scale dependent blender systems and bypassing the mill.

For use of the milled powdered media a solvent, preferably water (most particularly distilled and/or deionized water or purified water or water for injection) or an aqueous buffer is added to the media and the components are mixed until the medium is totally dissolved in the solvent.

The solvent may also comprise saline, soluble acid or base ions providing a suitable pH range (typically in the range between pH 1.0 and pH 10.0), stabilizers, surfactants, preservatives, and alcohols or other polar organic solvents.

It is also possible to add further substances like buffer substances for adjustment of the pH, fetal calf serum, sugars etc., to the mixture of the cell culture medium and the solvent. The resulting liquid cell culture medium is then contacted with the cells to be grown or maintained.

The present invention is further directed to a process for culturing cells by
a) providing a bioreactor
b) dissolving a cell culture medium according to the present invention in a solvent
c) mixing the cells to be cultured with the dissolved cell culture medium
d) incubating the mixture of step c)

A bioreactor is any unit suitable for the culture of cells, like a bag, container, vessel or tank in which cells can be cultured. A bioreactor is typically sterilized prior to use. Incubation is typically done under suitable conditions like suitable temperature etc. A person skilled in the art is aware of suitable incubation conditions for supporting or maintaining the growth/culturing of cells.

The cell culture media of the present invention comprising amino acids of certain particle sizes show better dissolving properties compared to standard media which are produced by mixing all components and submitting them to milling. It is often possible to generate dry powder media according to the invention which can be easily dissolved in a suitable solvent whereby dry powder media of the same composition but not comprising the amino acids as particles of certain sizes show poor dissolution properties.

The entire disclosure of all applications, patents, and publications cited above and below, especially corresponding EP 14004169.0 filed Dec. 11, 2014, are hereby incorporated by reference.

EXAMPLES

TABLE 1

|  |  | Molarity (mM) |
|---|---|---|
| 1 | HEPES_CCM | 96 |
| 2 | L-ARGININE MONOHYDROCHLORIDE | 43 |
| 3 | L-LYSINE MONOHYDROCHLORIDE | 47 |
| 4 | PYRUVIC ACID SODIUM SALt | 68 |
| 5 | L-LEUCINE | 55 |
| 6 | POLOXAMER 188 | 0.6 |
| 7 | POTASSIUM CHLORIDE | 63 |
| 8 | L-SERINE | 44 |
| 9 | L-VALINE | 39 |
| 10 | SODIUM CHLORIDE | 79 |
| 11 | L-THREONINE | 38 |
| 12 | L-PROLINE | 34 |
| 13 | L-PHENYLALANINE | 23 |
| 14 | L-ISOLEUCINE | 28 |
| 15 | L-HISTIDINE MONOHYDROCHLORIDE MONOHYDRATE | 15 |
| 16 | MAGNESIUM CHLORIDE HEXAHYDRATE | 29 |
| 17 | DI-SODIUM HYDROGEN PHOSPHAT ANHYDROUS | 18 |
| 18 | SODIUM DIHYDROGEN PHOSPHATE MONOHYDRATE FOR THE PRODUCTION OF CCM | 18 |
| 19 | MYO-INOSITOL | 13 |
| 20 | L-CYSTEINE HYDROCHLORIDE MONOHYDRATE | 13 |
| 21 | L-METHIONINE | 15 |
| 22 | CHOLINE CHLORIDE | 13 |
| 23 | L-TRYPTOPHAN | 8 |
| 24 | MAGNESIUM SULFATE ANHYDROUS | 9 |
| 25 | L-GLUTAMIC ACID | 4 |
| 26 | GLYCINE | 7 |
| 27 | HYPOXANTHINE MONOSODIUM | 2 |
| 28 | L-ALANINE | 4 |
| 29 | L-ASPARTIC ACID | 2 |
| 30 | CALCIUM CHLORIDE ANHYDROUS | 3 |
| 31 | FOLIC ACID | 0.5 |
| 32 | CALCIUM-D(+) PANTOTHENATE PH EUR, BP, USP, JP, FCC | 0.5 |
| 33 | VITAMIN B12 (CYANOCOBALAMINE) MICRONIZED | 0.09 |
| 34 | THIAMINE CHLORIDE HYDROCHLORIDE | 0.34 |
| 35 | 2'-DEOXYTHYMIDINE | 0.38 |
| 36 | NICOTINAMIDE | 0.63 |
| 37 | PYRIDOXAL HYDROCHLORIDE | 0.35 |

A dry powder cell culture medium with a composition according to table 1 is produced by mixing all components and milling them in a pin mill (UPZ100, at 19200 rpm)

A dry powder cell culture medium with the same composition is prepared according to the present invention. Especially if higher concentrated media formulations from the above recipe are produced the achieved liquid media when using the amino acids in particle sizes according to the present invention show a lower turbidity

The invention claimed is:

1. A dry powder cell culture medium in which more than 70% (w/w) of all cysteine, cystine and tyrosine present in the medium is present in the form of particles with particle sizes below 50 μm and in which more than 70% (w/w) of all serine, isoleucine, leucine, glycine and phenylalanine present in the medium is present in the form of particles with particle sizes above 100 μm.

2. The dry powder cell culture medium according to claim 1, wherein more than 75% (w/w) of all arginine, aspartic acid, glutamic acid and threonine present in the medium is present in the form of particles with particle sizes of between 50 and 150 μm.

3. The dry powder cell culture medium according to claim 1, wherein the cell culture medium is a mammalian cell culture medium.

4. The dry powder cell culture medium according to claim 1, wherein the cell culture medium is a chemically defined cell culture medium.

5. The dry powder cell culture medium according to claim 1, wherein at least 70% of all cysteine, cystine and tyrosine present in the medium is present in the form of particles with particle sizes between 10 and 50 μm.

6. The dry powder cell culture medium according to claim 1, wherein at least 70% of all histidine present in the medium is present in the form of particles with particle sizes between 25 and 100 μm.

7. The dry powder cell culture medium according to claim 1, wherein 70% (w/w) of all other amino acids present in the medium beside cysteine, cystine, tyrosine, histidine, arginine, aspartic acid, glutamic acid and threonine, are present in the form of particles with particle sizes above 100 μm.

8. A method for producing a cell culture medium comprising
    a) providing cysteine, cystine and tyrosine in the form of particles of which more than 70% (w/w) have particle sizes below 50 μm and serine, isoleucine, leucine, glycine and phenylalanine in the form of particles of which more than 70% (w/w) have particle sizes above 100 μm;
    b) providing all other media components beside the ones provided in step a) and mixing, sieving and milling them; and
    c) mixing the components provided in step a) and step b).

9. A process for culturing cells by
    a) providing a bioreactor;
    b) dissolving the dry powder cell culture medium according to claim 1 in a solvent;
    c) mixing the cells to be cultured with the dissolved cell culture medium of step b); and
    d) incubating the mixture of step c) in the bioreactor.

10. A process for culturing cells by
    a) dissolving the dry powder cell culture medium according to claim 1 in a solvent;
    b) mixing the cells to be cultured with the dissolved cell culture medium of step b); and
    c) incubating the mixture of step c) in a bioreactor.

* * * * *